United States Patent
Jansson et al.

(10) Patent No.: US 8,104,605 B2
(45) Date of Patent: Jan. 31, 2012

(54) MATERIAL SAMPLE COLLECTOR

(76) Inventors: Claes E. Jansson, Sacramento, CA (US); Tord L. Holmqvist, Woodland, CA (US)

(*) Notice: Subject to any disclaimer, the term of this patent is extended or adjusted under 35 U.S.C. 154(b) by 177 days.

(21) Appl. No.: 12/662,230

(22) Filed: Apr. 6, 2010

(65) Prior Publication Data

US 2011/0011702 A1    Jan. 20, 2011

Related U.S. Application Data

(60) Provisional application No. 61/213,776, filed on Jul. 14, 2009.

(51) Int. Cl.
*B65G 47/82* (2006.01)
(52) U.S. Cl. ............ 198/598; 198/820; 198/457.07
(58) Field of Classification Search .............. 198/638, 198/642, 598, 820, 821, 457.07
See application file for complete search history.

(56) References Cited

U.S. PATENT DOCUMENTS

| | | | |
|---|---|---|---|
| 3,570,648 A * | 3/1971 | Gillespie et al. ............ 198/598 |
| 3,718,819 A * | 2/1973 | Miksitz ........................ 198/820 |
| 3,923,169 A | 12/1975 | Van Drie |
| 4,250,017 A | 2/1981 | Reale |
| 4,303,506 A | 12/1981 | Finlay |
| 4,330,904 A | 5/1982 | Lambert |
| 4,345,655 A | 8/1982 | Fahrenholz |
| 4,541,532 A * | 9/1985 | Wilson ........................ 198/598 |
| 4,881,819 A | 11/1989 | Blees |
| 5,477,926 A | 12/1995 | Lizotte et al. |
| 5,667,298 A * | 9/1997 | Musil et al. ..................... 366/18 |
| 6,433,338 B1 * | 8/2002 | Nordbryhn et al. ...... 250/339.12 |
| 6,533,944 B1 | 3/2003 | Rohr |
| 6,854,587 B2 * | 2/2005 | Handel et al. ................. 198/598 |
| 7,131,538 B2 | 11/2006 | Johannsen |
| 2007/0272776 A1 | 11/2007 | Schenk |
| 2008/0200104 A1 | 8/2008 | Chuang |

OTHER PUBLICATIONS

Website, http://www.astecinc.com/index.php?option=com_content&view=article&id=660&Itemid=..., Astec Accu-Swipe® Automatic Belt Sweeper, two sheets printed from the internet on Jun. 23, 2009.
Website, http://www.intersystems.net/midbelt.asp, InterSystems sampler, two sheets printed from the internet on Jun. 23, 2009.

* cited by examiner

*Primary Examiner* — James R Bidwell
(74) *Attorney, Agent, or Firm* — Richard C. Litman

(57) ABSTRACT

The material sample collector is adapted to divert a sample of material from a trough conveyor for analysis of the sample. The collector includes at least one, and preferably two or more, laterally offset wheels rotating on axles. The wheels are in a vertical plane forming an acute dihedral angle with a vertical plane in which the central longitudinal axis of the conveyor is disposed. Each wheel subtends an elliptical segment extending across a portion of the width of the conveyor when viewed from an end of the conveyor. A sample chute extends laterally from the conveyor. The wheels are normally raised above the conveyor and its contents, and lowered when a sample is taken. The lowered wheels bear against the conveyor and/or its contents, diverting material from the conveyor onto a chute. The device is preferably manually operated, but may be powered and automated.

19 Claims, 7 Drawing Sheets

US 8,104,605 B2

MATERIAL SAMPLE COLLECTOR

CROSS-REFERENCE TO RELATED APPLICATION

This application claims the benefit of U.S. Provisional Patent Application Ser. No. 61/213,776, filed Jul. 14, 2009.

BACKGROUND OF THE INVENTION

1. Field of the Invention

The present invention relates to conveyor systems, and particularly to a material sample collector for periodically diverting a sample of material (dirt, gravel, or other material) from a conveyor for inspecting the quality of the material.

2. Description of the Related Art

The conveyance of materials (e.g., sand and gravel, articles of manufacture and components on production lines, food products during processing, etc.) by means of conveyor belt systems of various types is well known. From time to time it is necessary to take a sample of the conveyed product for testing, quality measurement, and/or for some other purpose(s). This is often done manually, although some automated devices for taking samples are also known.

The sand and gravel mining industry is an example of a field in which it is necessary to take periodic samples of material. The material must be sampled periodically to determine its purity, i.e., to confirm that there is not an excessive amount of foreign matter (dirt, vegetation, etc.) mixed in with the sand or gravel, and/or to determine the particle size of the gravel or sand. Conventionally, this requires shutting down the conveyor line for some period of time while a sample is withdrawn manually from the conveyor. Obviously, this is an inefficient process when the entire conveyor line must be stopped from time to time for material sampling.

As a result, various devices have been developed to take a conveyed sample automatically from a moving conveyor line. However, such automated sampling devices are universally complex and costly, and require considerably more maintenance (and upkeep expense) than do simpler manual systems, even though such manual systems require that the conveyor line be shut down for sampling.

Thus, a material sample collector solving the aforementioned problems is desired.

SUMMARY OF THE INVENTION

The material sample collector enables a person to collect a sample of material from a moving trough belt conveyor system without shutting down the conveyor line. The collector preferably has two or more wheels free to rotate on axles aligned at an acute angle to the longitudinal axis of the conveyor system. The result is that each of the wheels subtends an elliptical section when viewed along the longitudinal axis of the conveyor, and does not span the entire width of the conveyor. Preferably, an upstream wheel is laterally offset to the side of the conveyor opposite the sample chute, and a downstream wheel is laterally offset to the side of the conveyor having the sample chute.

The wheels are normally raised to allow the product (gravel, sand, etc.) to be carried unimpeded along the moving conveyor line. When the wheels are lowered into the conveyor trough, the wheels are rotated by contact with the moving belt and/or by the material being conveyed by the belt system. The upstream wheel diverts material around the wheel from one edge of the conveyor toward the center of the conveyor, where the diverted material is intercepted by the downstream wheel. The downstream wheel then diverts the material further to spill from the trough belt and into the sample chute or other collection device extending from the belt and generally between the two wheels.

The sampler wheels are preferably manually controlled and normally held above the conveyor trough by a spring or counterweight, whereupon the operator may pull the wheels down manually to divert a sample from the conveyor. Alternatively, the mechanism may be actuated by pneumatic, hydraulic, or electrical power means, with such actuation being controlled remotely either by an operator or automatically by a timer or other actuation means.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The material sample collector periodically collects or diverts a sample of material from a conveyor line. The sample collector is particularly well suited for use in the sand and gravel mining industry, where such materials are transported from the pit via a conveyor belt or line for delivery to other transportation or storage. However, the material sample collector is adaptable for use in collecting or diverting a sample of virtually any material, particularly aggregate material, that may be carried on a conveyor belt or conveyor system.

Figure 1:
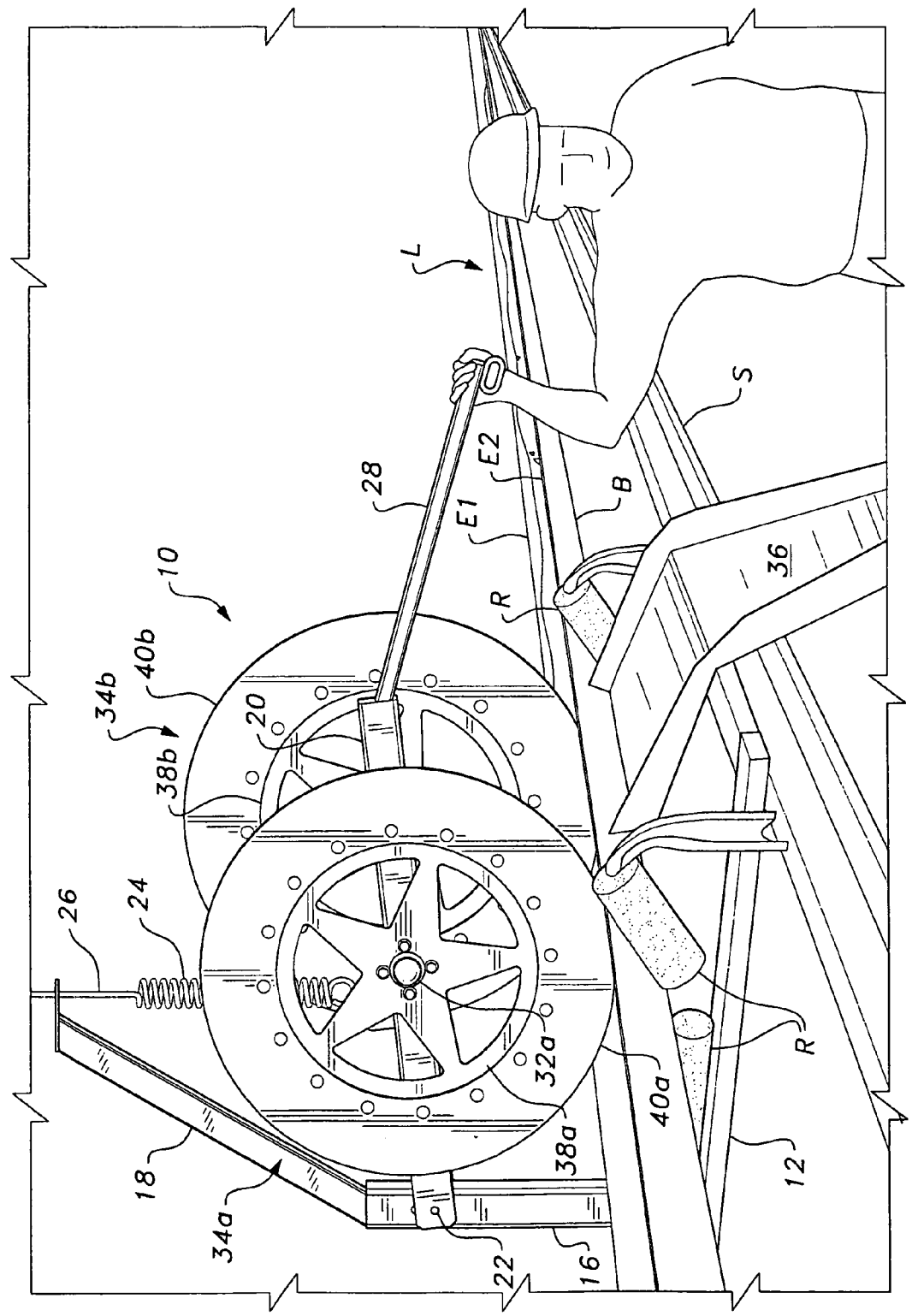
FIG. 1 is an environmental, perspective view of a material sample collector according to the present invention, showing its operation and use.

FIG. 1 of the drawings provides an environmental perspective view of a first embodiment of the material sample collector (or collector) 10 installed along a conveyor line L. The conveyor line or conveyor L includes a support structure S having a series of conveyor belt support rollers R mounted thereon. The rollers R include first and second side rollers having their rotational axes inclined upwardly and outwardly from the conveyor line and central rollers having generally horizontal rotational axes, generally as shown in FIGS. 2, 3, 6, and 7. This results in the first and second edges E1 and E2 of the conveyor belt B being raised relative to the center of the belt, with the belt B forming a trough configuration to prevent the spillage of loose or aggregate material carried thereon.

The material sample collector 10 includes a frame 12 that is secured across the support structure S of the conveyor L beneath the conveyor belt B. The collector frame 12 may be secured to the conveyor support structure S by means of clamps C (shown in FIGS. 2, 3, 6, and 7) or other conventional means (e.g., welding, bolting, etc.). One or more sockets or receptacles 14 (e.g., FIG. 2) extend upwardly from the collector frame 12 outboard of the conveyor belt B when the sample collector 10 is secured to the conveyor line L. The socket(s) or receptacle(s) 14 is/are preferably formed of stock having a non-circular cross section, e.g., square tubing, in order for a correspondingly sectioned post 16 to fit closely therein without rotating within the socket 14. The socket(s) or post receptacle(s) 14 are oriented at an angle to the sample collector frame 12, and thus to the support structure S and longitudinal axis A (shown in FIG. 4) of the conveyor line L, i.e., it is not square with the sides of the collector frame 12 or with the conveyor line support structure S. The reason for this arrangement is explained further below.

Figure 4:
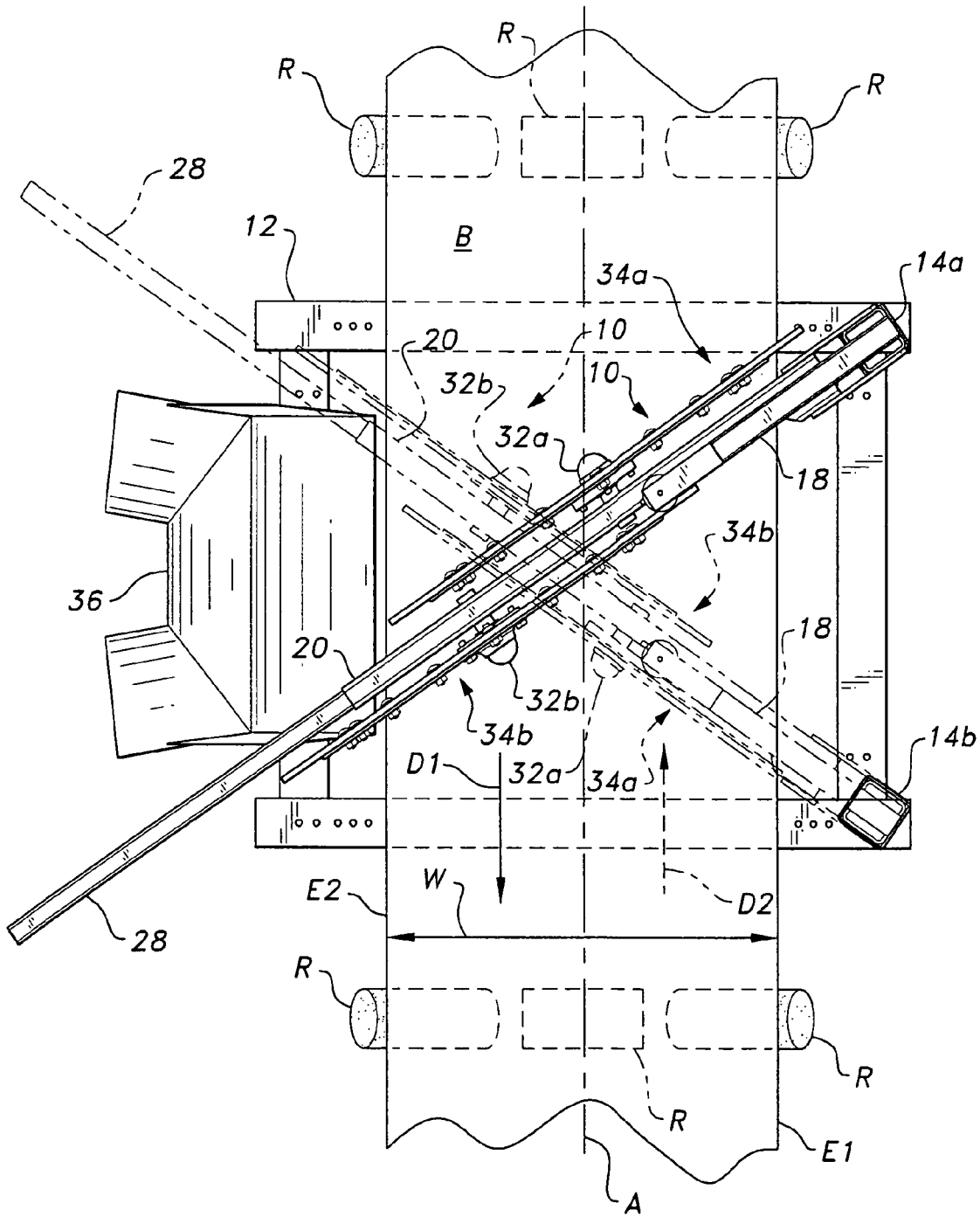
FIG. 4 is a top plan view of the material sample collector of FIG. 1 disposed across the conveyor.

A post 16 is immovably affixed (e.g., bolted, etc.) to the socket 14 and extends upwardly therefrom. Preferably, the post 16 is attached to the socket 14 with bolts, pins, or other conventional removable fasteners to allow the post 16 to be removed and repositioned. Alternatively, the base or attachment end of the post 16 may be welded or otherwise directly affixed to the collector frame 12, if so desired, obviating the need for the socket 14. A lift boom 18 is immovably affixed to and extends from the top of the post 16 at an angle thereto in order to position the upper or distal portion of the lift boom 18 over the conveyor belt B. The lift boom 18 extends across the conveyor belt B at an acute angle (i.e., less than 90°) to the longitudinal axis A of the conveyor line L, as shown in FIG. 4 of the drawings, in order to support additional underlying structure, as described further below.

An arm 20 is attached to the post 16 by a pivot 22, and pivots through an arc substantially directly below the lift boom 18. Thus, the pivot arm 20 is also disposed at an acute angle to the longitudinal axis A of the conveyor line L, as shown in FIG. 4. The dihedral angle between the plane of the lift boom 18 and pivot arm 20 and the plane of the underlying longitudinal axis A of the conveyor belt B is preferably between 28° and 38°, but may be adjusted as needed.

Figure 6:
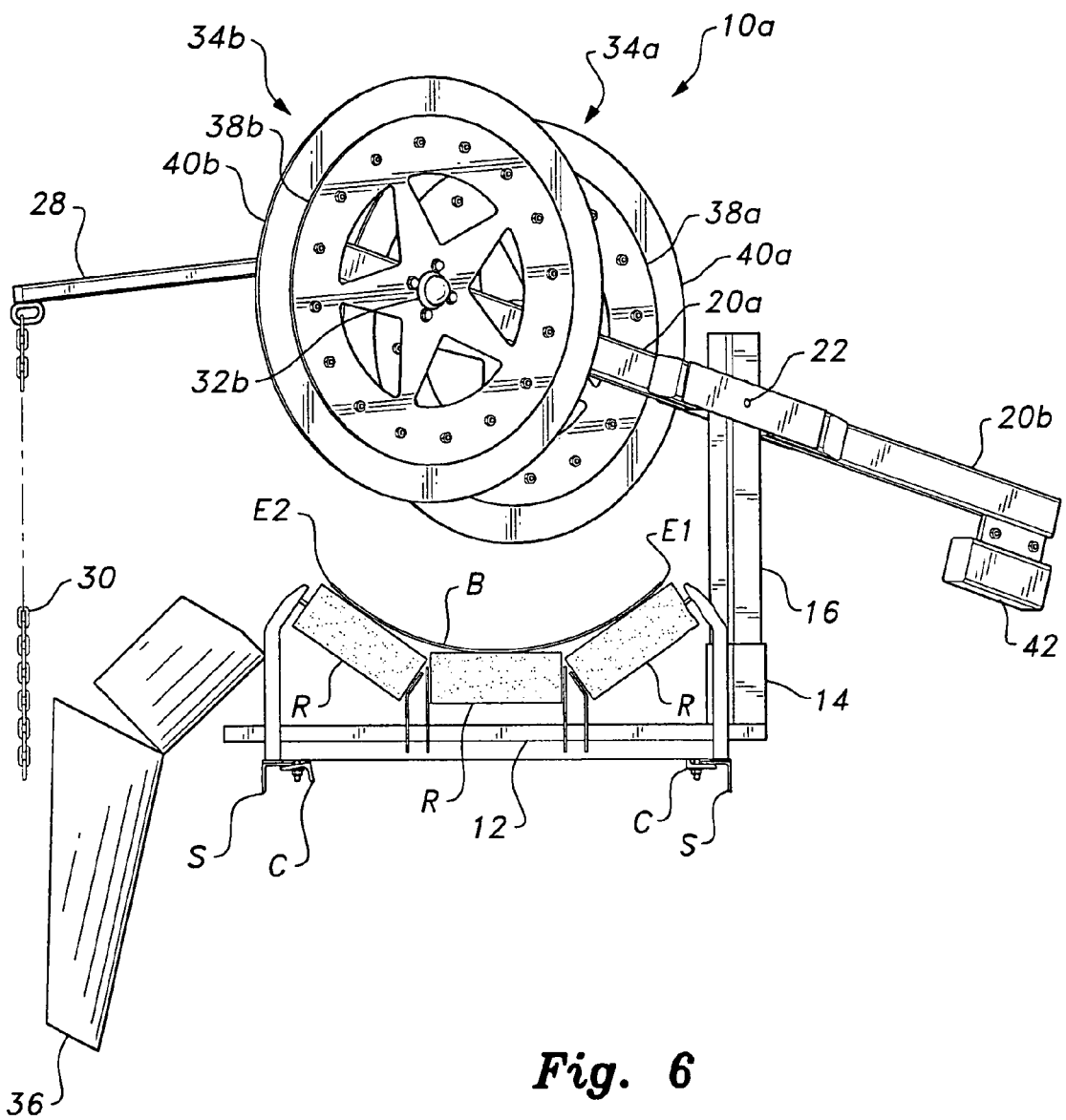
FIG. 6 is an end elevation view of a conveyor incorporating an alternative embodiment of a material sample collector according to the present invention.
Figure 7:
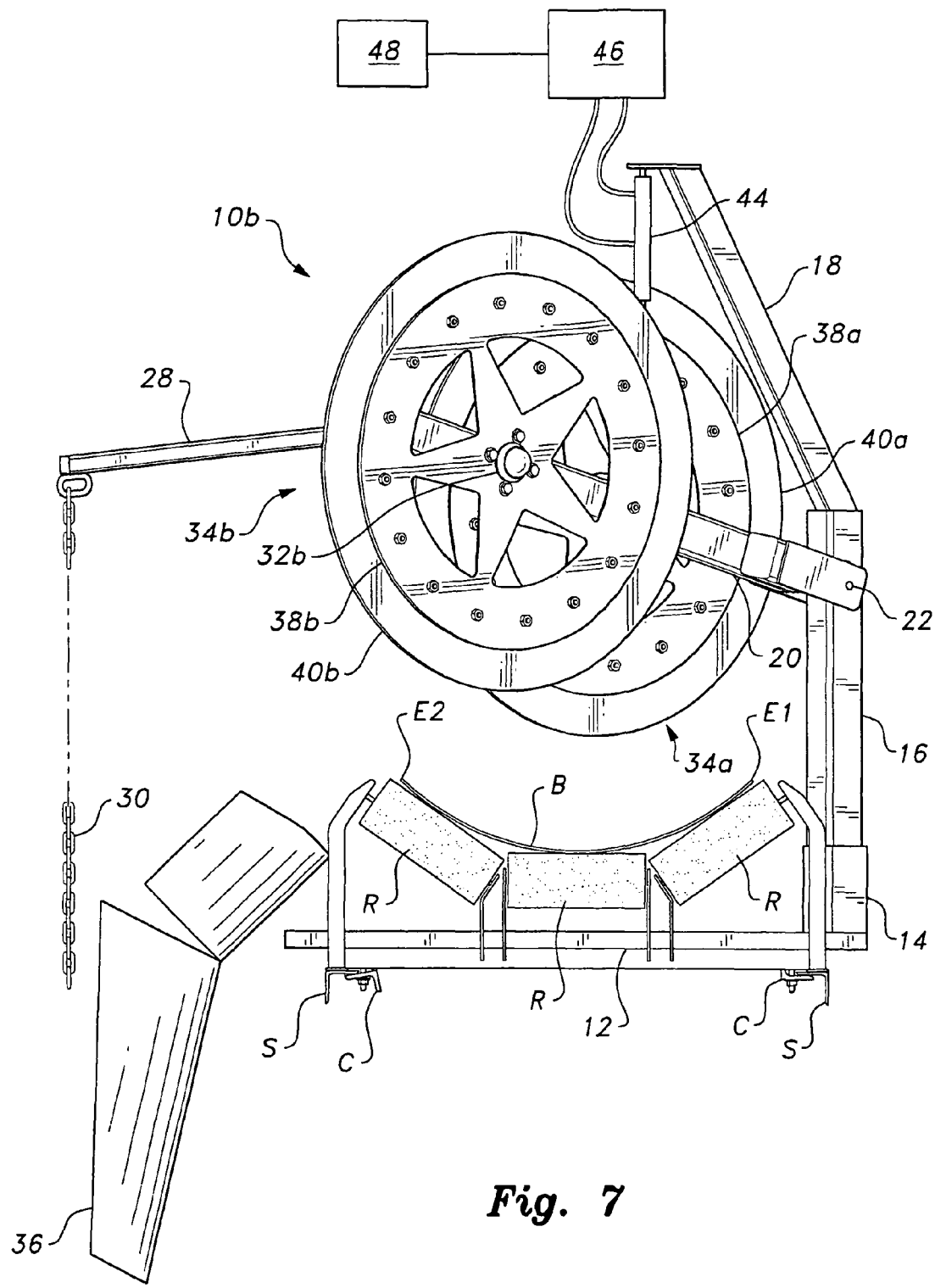
FIG. 7 is an end elevation view of a conveyor incorporating another alternative embodiment of a material sample collector according to the present invention.

The distal portion of the arm 20 is suspended from the lift boom 18 by a helical spring 24 that holds the arm 20 (and other components attached thereto) above the conveyor belt B. The precise height of the pivot arm 20 may be adjusted by means of a threaded rod 26 connecting the top of the spring 24 to the lift boom 18. Alternatively, other means of suspending the arm 20 above the conveyor belt B may be provided in other embodiments of the sample collector, as shown in FIGS. 6 and 7 and described in detail further below.

The arm 20 includes a handle 28 extending from its distal end, i.e., opposite the pivot 22 end thereof. Alternatively, a chain 30, or cord, rope, etc., may be attached to the distal end of the handle 28, as shown in FIGS. 2, 3, 6, and 7, to allow an operator to pull the arm 20 downward in an elevated conveyor installation where the handle 28 is not immediately accessible from ground level.

The pivot arm 20 includes at least one axle extending laterally therefrom for the attachment of a wheel thereto. Most preferably a plurality of axles, e.g., two, are provided, as shown in the drawings. The two axles 32a, 32b (shown together in the plan views of FIGS. 4 and 5) are offset from one another along the length of the pivot arm 20 and extend to opposite sides of the pivot arm 20, and are thus laterally offset from one another relative to the width W (as defined by the first and second edges E1 and E2) of the conveyor belt B. The reason for this is explained further below. The axles 32a, 32b are substantially normal to the length of the pivot arm 20 from which they extend, and thus also form an acute angle with the longitudinal axis A of the conveyor belt B when viewed from above the conveyor belt B.

Each of the axles 32a, 32b has a wheel 34a, 34b, rotatably attached thereto. The wheels 34a, 34b are disposed above the trough belt B of the conveyor system. As the wheels rotate upon their respective axles 32a, 32b and the axles form acute angles relative to the longitudinal axis of the conveyor belt, the planes of rotation of the wheels also form an acute angle with the plane of the central longitudinal axis of the belt, as shown in FIG. 4 of the drawings. The wheels 34a, 34b are oriented in a "downstream" direction, i.e., the pivot arm 20 to which they are attached extends from the direction of pickup of the belt B and across the belt toward the direction of delivery, as indicated by the solid line directional arrow D1 in FIG. 4.

It will be noted in FIG. 4 that two sockets or receptacles are provided for the installation of the post 16, with the two sockets or receptacles being designated as sockets 14a (upstream) and 14b (downstream). This construction allows the post 16 to be installed in either socket according to the direction of travel of the belt B. An alternative position for the post 16 and its lift boom 18, pivot arm 20, axles 32a and 32b, and wheels 34a and 34b is shown in broken lines in FIG. 4, for use when the conveyor belt B is running in the direction shown by the broken line directional arrow D2.

Figure 5:
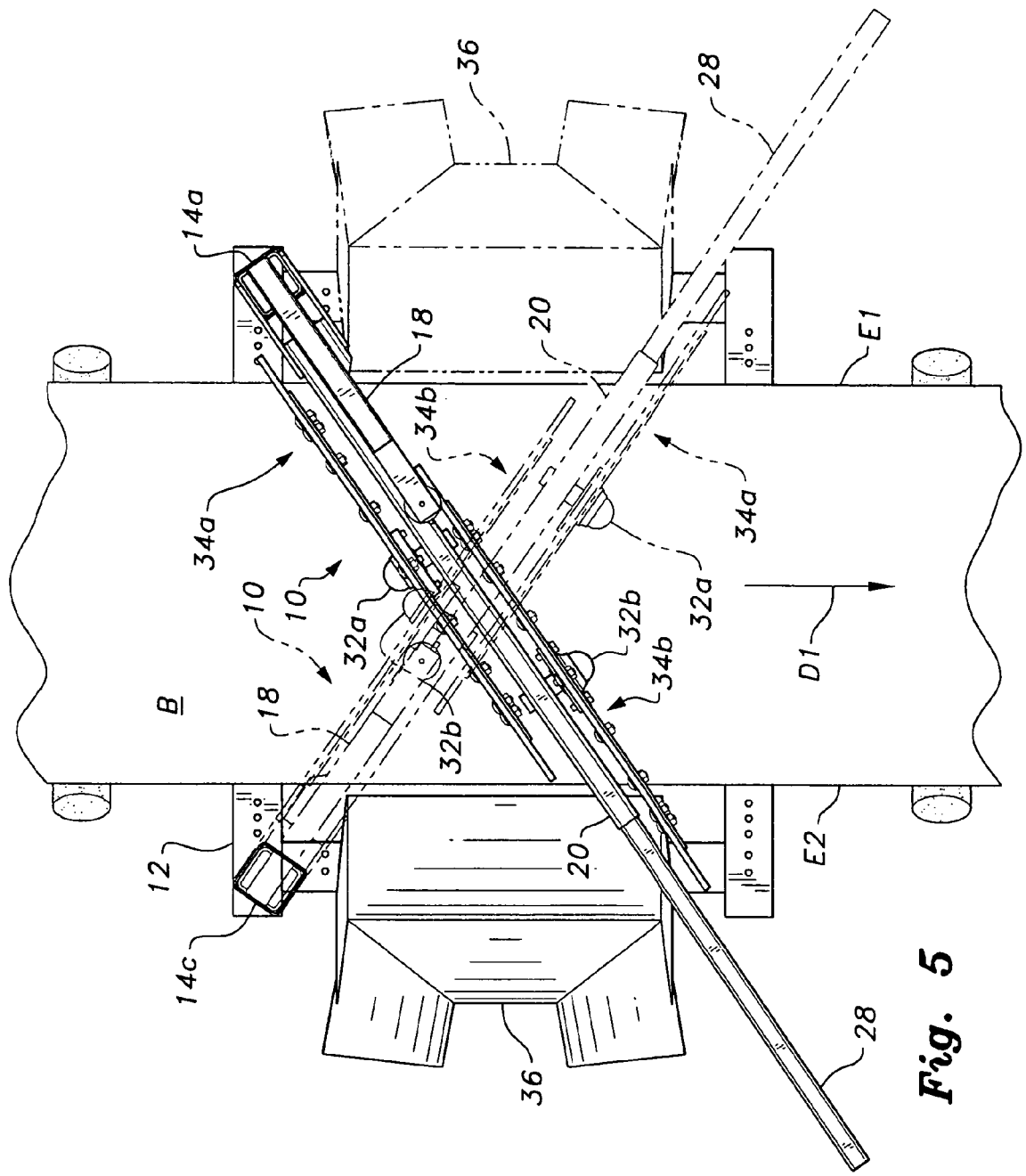
FIG. 5 is a top plan view of the material sample collector of FIG. 1 disposed across the conveyor from the opposite side of that shown in FIG. 4.

FIG. 5 illustrates another alternative position or installation for the sample collector 10, wherein a third post receptacle 14c is provided to the opposite side of the conveyor belt B from the first receptacle 14a. A fourth post receptacle (not shown) may be installed to the same side of the frame 12 as the receptacle 14c, if desired, to provide additional versatility in orienting the sample collector 10 as needed. In the case of FIG. 5, the material sample collector 10 is shown in solid lines in the same orientation as that shown in FIGS. 1 through 3 and in FIG. 4 in solid lines, as well as in FIGS. 6 and 7, i.e., with the post installed in the first socket or receptacle 14a adjacent the first edge E1 of the conveyor belt B. An alternative installation is shown in broken lines in FIG. 5, with the post installed in the alternative socket or receptacle 14c adjacent the second edge E2 of the conveyor belt B. The chute 36 extends from the opposite side of the belt B from the receptacle used to attach the post 16 and the remainder of the sample collector assembly, in each case.

Figure 2:
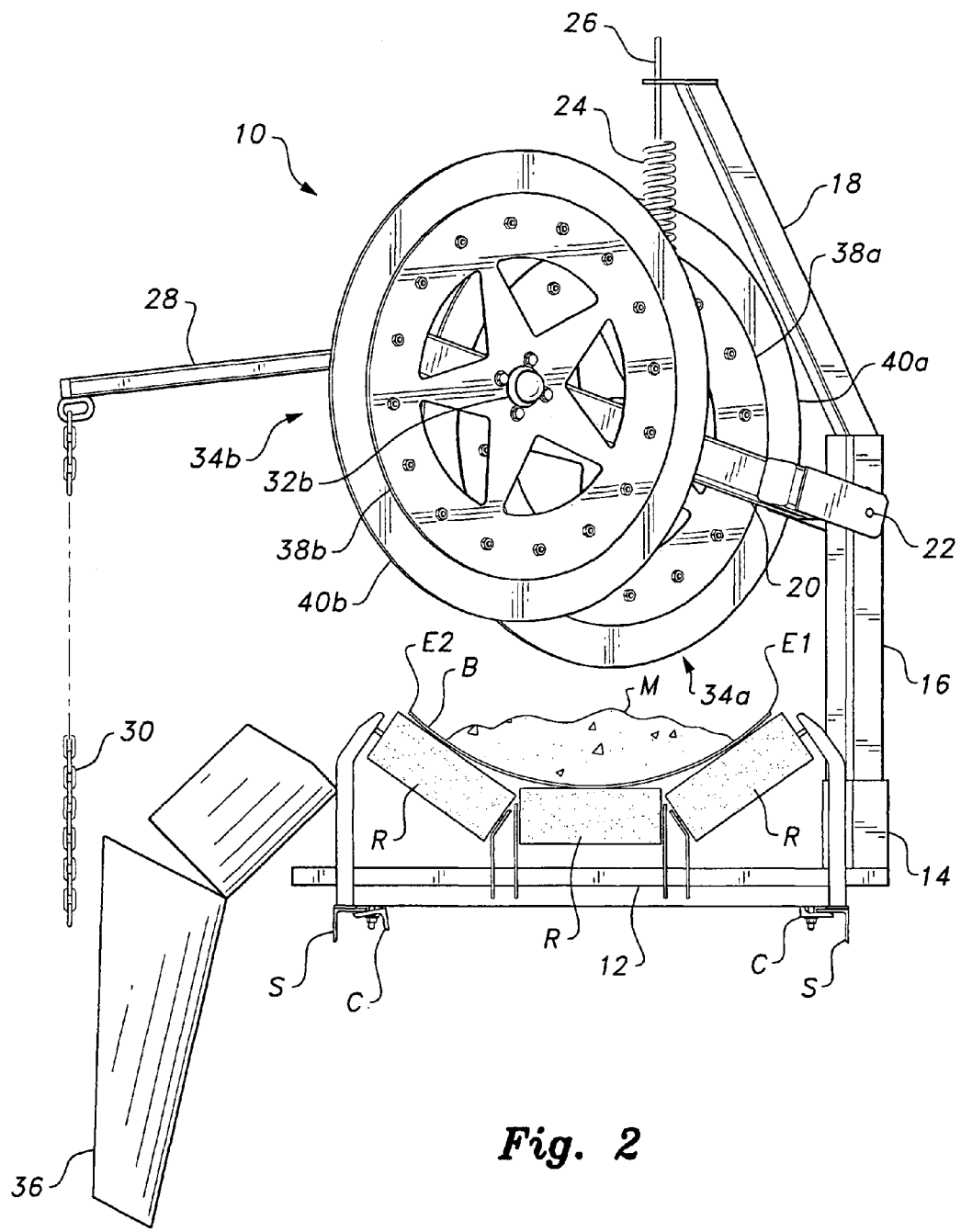
FIG. 2 is an end elevation view in section of a conveyor incorporating a material sample collector according to the present invention, with the collector shown in a raised and inoperative position.
Figure 3:
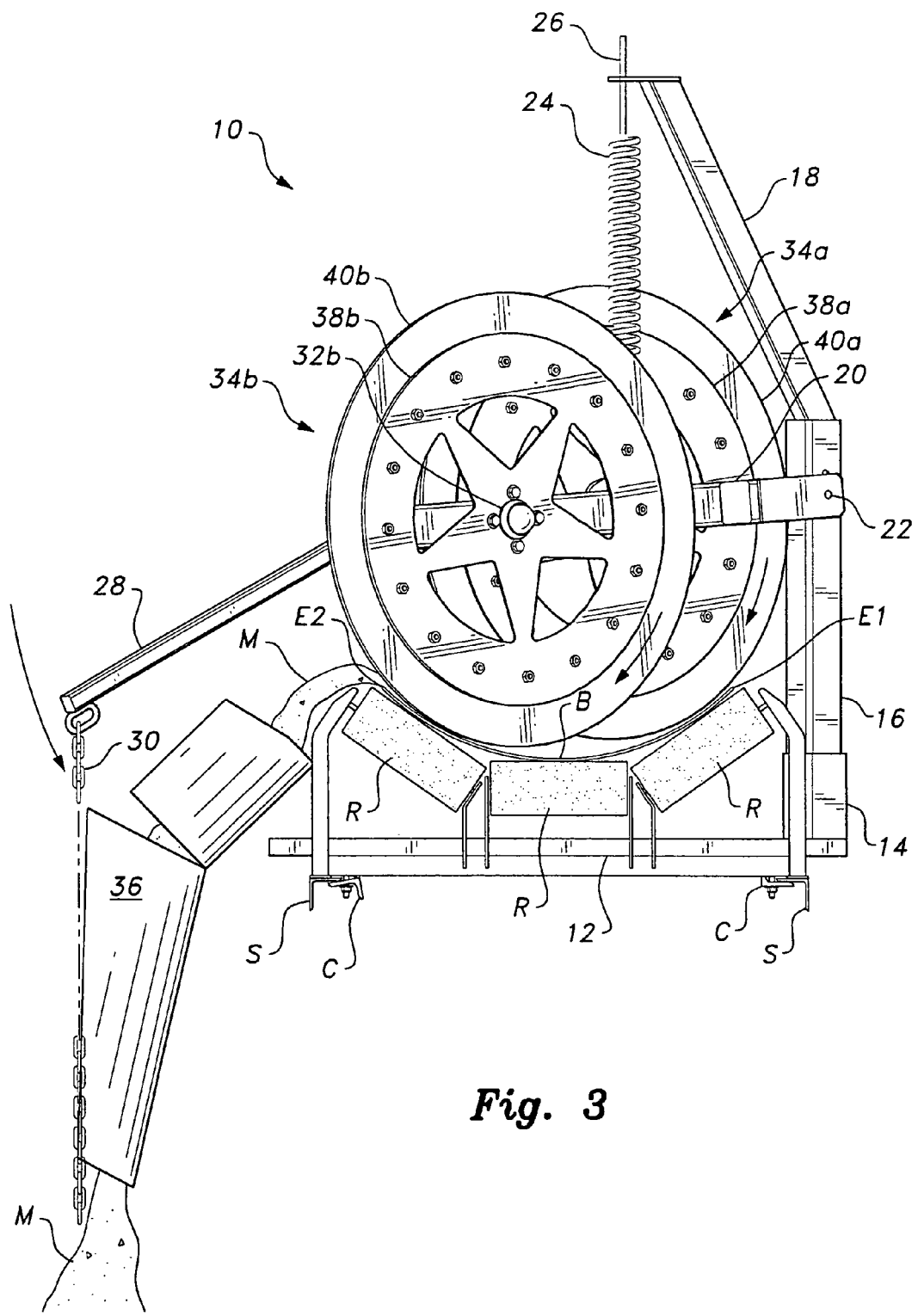
FIG. 3 is an end elevation view in section of a conveyor incorporating a material sample collector according to the present invention, showing the collector lowered to divert a sample from the conveyor.

FIGS. 2 and 3 provide end elevation views in section of the conveyor line L and its trough belt B, and respectively show the pivot arm 20 and wheel assembly 34a, 34b in a raised position in FIG. 2 and lowered in FIG. 3. It was noted further above that a plurality of wheels is preferably installed on the pivot arm 20, with the axles of those wheels being laterally offset or staggered relative to the width of the conveyor belt B. This is due to the angle of the wheels 34a, 34b relative to the longitudinal axis A of the conveyor belt B. It will be noted in FIGS. 2 and 3 that the two wheels 34a, 34b appear as ellipses as viewed from the end of the conveyor belt B due to their angles relative to the conveyor run. Thus, even if the wheels 34a, 34b have diameters equal to the curvature of the inside of the trough belt B, they cannot contact the complete width of the inside of the belt.

Accordingly, the lateral offset of the "upstream" wheel 34a toward the first edge E1 of the belt B results in the periphery or rim of that wheel contacting only a portion of the belt B near the first edge E1 thereof when the wheels 34a and 34b are lowered to the position shown in FIG. 3. Material M contacting the first or upstream wheel 34a is diverted toward the second edge E2 of the belt, but is free to flow between the edge of the upstream wheel 34a and the second edge E2 of the belt B. However, the "downstream" or second wheel 34b is also in contact with the belt B toward the second edge E2 of the belt. Thus, the material M that flows around the first or upstream wheel 34a is diverted toward the second edge E2 of the belt B, whereupon it contacts the rim of the second wheel 34b and is diverted further toward and over the second edge E2 of the belt B. A collection chute 36 is placed where the material M is diverted over the edge of the belt B.

The two wheels 34a, 34b are not powered and are free to rotate upon their respective axles 32a, 32b when acted upon by some rotational force. As the rotation planes of the two wheels are at an acute angle to the belt B, contact with the belt B (and/or with material M carried in the belt B) will drive the wheels to rotate toward the "downstream" direction of travel of the conveyor belt B, i.e., from the first edge E1 toward the second edge E2 of the belt B as shown by the rotation arrows in the example shown in FIG. 3. This assists further in the diversion of material M from the trough of the belt, over the second edge E2, and into the chute 36 for gathering a material sample. Preferably, each of the wheels 34a, 34b includes a rigid central disc 38a, 38b, (metal plate, etc.) with a plastic rim 40a, 40b, extending therefrom. The use of a plastic material for the rim 40a, 40b reduces wear upon the surface of the belt B when the wheels 34a, 34b are lowered to gather a sample.

The arm 20 with its wheels 34a, 34b is normally suspended above the trough belt B and any material M therein by the tension of the spring 24. This allows the belt B to carry the material M unimpeded to its destination, as shown in FIG. 2. When it is desired to take a sample of the material M, the operator need only pull down on the handle 28 (or the chain, rope, or cord 30) to lower the pivot arm 20 and its wheels 34a, 34b against the spring 24 tension, and into the trough belt B and its material contents M, generally as shown in FIG. 1. When this occurs some of the material M will be diverted laterally from the belt B and into the chute 36, as shown in FIG. 3 and described above.

FIG. 6 illustrates alternative means for holding the pivot arm and its wheels above the conveyor and material therein. In FIG. 6, an alternative pivot arm 20a includes a counterweight extension 20b opposite the portion of the arm extending over the conveyor belt B to which the axles 32a, 32b and wheels 34a, 34b are attached. A counterweight 42 sufficient to overbalance the weight of the opposite portion of the arm 20a and its wheels 34a, 34b and other structure, is installed on the counterweight extension 20b of the arm 20a. This eliminates the need for the lift boom 18 and spring 20, although it requires somewhat more room laterally from the conveyor line for the counterweight extension 20b of the arm 20a and its counterweight 42.

FIG. 7 illustrates a material sample collector embodiment 10b wherein the lifting of the pivot arm 20 and its wheels 34a, 34b is accomplished by a powered actuator 44 in lieu of the spring 24 of the embodiment of FIGS. 1 through 5. A power source or supply 46 communicates with the actuator 44 to operate the actuator and lift the pivot arm 20 and wheels 34a, 34b. The actuator 44 may comprise a pneumatically actuated strut that is plumbed to retract when pressure is applied thereto by the power source 46. Alternatively, the actuator 44 may be a hydraulic strut, with the power source or supply 46 supplying hydraulic fluid under pressure to the strut or actuator 44. Another alternative arrangement may comprise an electrically powered jackscrew for the actuator 44, with the power supply or source 46 providing electrical power. The sampling process may be completely automated when powered means is provided to operate the sample collector 10b, with a controller 48 actuating the power source to provide the required power to the corresponding actuator 44. The controller 48 may be a timer or may actuate the power source 46 according to other parameters, e.g., the speed of the conveyor belt B, the amount of material carried on the belt B, and/or some other quality (moisture, etc.) that may be detected. Sensors for detecting all of the above parameters are well known and conventional, and need not be described in detail. The added complexity and expense of such an automated sample collector 10b may be considered worthwhile in certain installations where a human operator is not available at times when sampling is desired, and/or where the sample collector must be located where it is difficult or impossible for a human operator to routinely actuate the device.

Accordingly, the material sample collector in its various embodiments provides a simple and economical means for material handlers to check samples of the material being conveyed without need to shut down the conveyor line. While the sample collector may be installed and used in virtually any conveyor line that conveys virtually any type of material, it is particularly well suited for installation and use on conveyors used in the sand and gravel industry. The ability to run the conveyor line continuously while simultaneously taking periodic samples of the material being conveyed provides a great economic advantage to operators of such lines.

It is to be understood that the present invention is not limited to the embodiments described above, but encompasses any and all embodiments within the scope of the following claims.

We claim:

1. A material sample collector for a conveyor, the conveyor having a support structure, a central longitudinal axis, and a trough belt adapted for the carriage of material thereon, the belt having a first edge, a second edge opposite the first edge, and a width therebetween, the material sample collector comprising:
    a frame adapted for attachment to the support structure of the conveyor to extend across and beneath the conveyor belt;
    a post extending upwardly from the frame;
    an arm pivotally attached to and extending from the post over the conveyor belt, the arm being disposed in a vertical plane forming an acute dihedral angle with a vertical plane containing the central longitudinal axis of the trough belt;
    at least one axle extending normal to the arm;
    a wheel rotationally disposed upon the axle, the arm being biased so that the wheel is normally above the trough belt, leaving flow of material on the belt unimpeded by the at least one wheel; and
    means for selectively lowering the wheel into the trough belt to drive the wheel in order to divert a sample of material from the trough belt.

2. The material sample collector according to claim 1, further including:
    a conveyor support structure; and
    a trough belt disposed upon the conveyor support structure, the trough belt being adapted for the carriage of material thereon, the trough belt having at least a central longitudinal axis, a first edge, a second edge opposite the first edge, and a width therebetween.

3. The material sample collector according to claim 1, wherein said at least one axle comprises a plurality of axles extending from the arm, each of the axles being laterally offset relative to the central longitudinal axis of the trough belt.

4. The material sample collector according to claim 1, wherein the wheel comprises a central disc having a plastic rim extending circumferentially therearound.

5. The material sample collector according to claim 1, further including:
   a lift boom extending from the post; and
   a spring extending from the lift boom to the arm, the spring biasing the arm to a lifted position above the trough belt.

6. The material sample collector according to claim 1, wherein the arm has an extension portion opposite the at least one axle, the material sample collector further comprising a counterweight disposed upon the extension portion of the arm, biasing the axle to a lifted position above the trough belt.

7. The material sample collector according to claim 1, further including:
   a lift boom extending from the post;
   a powered actuator extending between the lift boom and the arm; and
   a power supply communicating with the powered actuator.

8. A trough conveyor and material sampler therefor, comprising in combination:
   a conveyor support structure;
   a trough belt disposed upon the conveyor support structure, the trough belt being adapted for the carriage of material thereon, the trough belt having a central longitudinal axis, a first edge, a second edge opposite the first edge, and a width therebetween;
   a frame attached to the conveyor support structure, the frame extending across and beneath the trough belt;
   a post extending upwardly from the frame;
   an arm pivotally attached to and extending from the post and over the trough belt in a vertical plane forming an acute dihedral angle with a vertical plane in which the central longitudinal axis of the conveyor is disposed;
   at least one axle extending normal to the arm;
   a wheel rotationally disposed upon the axle above the trough belt; and
   means for selectively lowering the wheel into the trough belt to drive the wheel in order to divert a sample of material therefrom.

9. The material sample collector according to claim 8, wherein said at least one axle comprises a plurality of axles extending from the arm, each of the axles being laterally offset relative to the width of the trough belt.

10. The material sample collector according to claim 8, wherein the wheel comprises a central disc having a plastic rim extending circumferentially therearound.

11. The material sample collector according to claim 8, further including:
    a lift boom extending from the post; and
    a spring extending from the lift boom to the arm, the spring biasing the arm to a lifted position above the trough belt.

12. The material sample collector according to claim 8, wherein the arm has an extension portion opposite the axle, the material sample collector further comprising a counterweight disposed upon the extension portion of the arm, biasing the axle to a lifted position above the trough belt.

13. The material sample collector according to claim 8, further including:
    a lift boom extending from the post;
    a powered actuator extending between the lift boom and the arm; and
    a power supply communicating with the powered actuator.

14. A material sample collector for a conveyor, the conveyor having a support structure, a central longitudinal axis, and a trough belt adapted for the carriage of material thereon, the belt having a first edge, a second edge opposite the first edge, and a width therebetween, the material sample collector comprising:
    a frame adapted for attachment to the support structure of the conveyor, the frame extending across and beneath the trough belt;
    a post extending upwardly from the frame;
    an arm pivotally attached to and extending from the post over the belt of the conveyor;
    a plurality of axles extending normal to the arm, each of the axles being laterally offset from the arm;
    a wheel rotationally disposed upon each of the axles, the arm being biased above the trough belt; and
    means for selectively lowering the wheels into the trough belt to drive the wheels and divert a sample of material therefrom.

15. The material sample collector according to claim 14, further including:
    a conveyor support structure; and
    a trough belt disposed upon the conveyor support structure, the trough belt being adapted for the carriage of material thereon, the trough belt having at least a longitudinal axis, a first edge, a second edge opposite the first edge, and a width therebetween.

16. The material sample collector according to claim 14, wherein each of the wheels comprises a central disc having a plastic rim extending circumferentially therearound.

17. The material sample collector according to claim 14, further including:
    a lift boom extending from the post; and
    a spring extending from the lift boom to the arm, the spring biasing the arm to a lifted position above the trough belt.

18. The material sample collector according to claim 14, wherein the arm has an extension portion opposite the axle, the material sample collector further comprising a counterweight disposed upon the extension portion of the arm, biasing the axle to a lifted position above the trough belt.

19. The material sample collector according to claim 14, further including:
    a lift boom extending from the post;
    a powered actuator extending between the lift boom and the arm; and
    a power supply communicating with the powered actuator.

* * * * *